United States Patent [19]
Mo et al.

[11] Patent Number: 5,964,706
[45] Date of Patent: Oct. 12, 1999

[54] METHOD AND APPARATUS FOR PULSED DOPPLER IMAGING USING CODED EXCITATION ON TRANSMIT AND PULSE COMPRESSION ON RECEIVE

[75] Inventors: Larry Y. L. Mo, Waukesha; Richard Y. Chiao, Clifton Park, both of Wis.

[73] Assignee: General Electric Company, Milwaukee, Wis.

[21] Appl. No.: 09/040,968

[22] Filed: Mar. 18, 1998

[51] Int. Cl.$^6$ ........................................................ A61B 8/00
[52] U.S. Cl. ........................... 600/443; 600/442; 600/453; 600/455
[58] Field of Search ................... 600/443, 444, 600/447, 453, 455; 128/916

[56] References Cited

U.S. PATENT DOCUMENTS

| | | | |
|---|---|---|---|
| 4,888,744 | 12/1989 | Keeler | 367/90 |
| 5,582,176 | 12/1996 | Swerling et al. | 600/447 |
| 5,632,277 | 5/1997 | Chapman et al. | 128/660.07 |
| 5,706,819 | 1/1998 | Hwang et al. | 128/662.02 |
| 5,777,892 | 7/1998 | Nabity et al. | 600/455 |

OTHER PUBLICATIONS

Takeuchi, "Chirped Excitation for <100db Time Sidelobe Echo Sounding," Proc. 1995 IEEE Ultrasonics Symp., pp. 1309–1314.

Takeuchi, "Coded Excitation for Harmonics Imaging", Proc. 2996 IEEE Ultrasonics Symp., pp. 1433–1436.

Welch, "Pulse Compression Ultrasound for Minimization of Transmitted Peak Power", Proc. 20th Annual Northeast Bioengineering Conference, Springfield, MA.

Welch et al., "Sidelobe Suppressed Spread Spectrum Pulse Compression for Ultrasonic Tissue Imaging," IEEE Trans. Ultrasonics, Ferroelec. & Freq. Control (accepted for publication 1997).

Lee et al., "High–Speed Digital Golay Code Flaw Detection System," Proc. 1981 Ultrasonics Symp., pp. 888–891.

Hayward et al., "A Digital Hardware Correlation System for Fast Ultrasonic Data Acquisition in Peak Power Limited Applications," IEEE Trans. Ultrason. Ferroelec. Freq. Cont., vol. 35, No. 6, Nov. 1988, pp. 800–808.

Mayer et al., "Three–Dimensional Imaging System Based on Fourier Transform Synthetic Aperture Focusing Technique," Ultrasonics, vol. 28, Jul. 1990, pp. 241–255.

Takeuchi, "An Investigation of a Spread Energy Method for Medical Ultrasound Systems. II. Proposed System and Possible Problems," Ultrasonic, vol. 17, Sep. 1979, pp. 219–224.

O'Donnell, "Coded Excitation System for Improving the Penetration of Real–Time Phased–Array Imaging Systems," IEEE Trans. Ultrason. Ferroelec. Freq. Cont., vol. 39, No. 3, May 1992, pp. 341–351.

*Primary Examiner*—Francis J. Jaworski
*Assistant Examiner*—Maulin Patel
*Attorney, Agent, or Firm*—Dennis M. Flaherty; Christian G. Cabou; Phyllis Y. Price

[57] ABSTRACT

A pulsed Doppler technique uses coded excitation on transmit and pulse compression on receive. Coded excitation allows a long transmit pulse to be compressed on receive such that most energy is concentrated in a short interval. In the case of a single coded transmit for each transmit focal position, the receive signals are compressed utilizing matched or mismatched filtering. In the case of a two or more coded transmits for each transmit focal position, the receive signals are compressed utilizing filtering coefficients which match the respective transmit codes during each firing. These techniques can be used to maximize Doppler sensitivity of a small but deep-lying sample volume. Alternatively, for a given transmit acoustic burst length and dosage, the sample volume can be reduced to achieve better spatial resolution without compromising sensitivity.

21 Claims, 4 Drawing Sheets

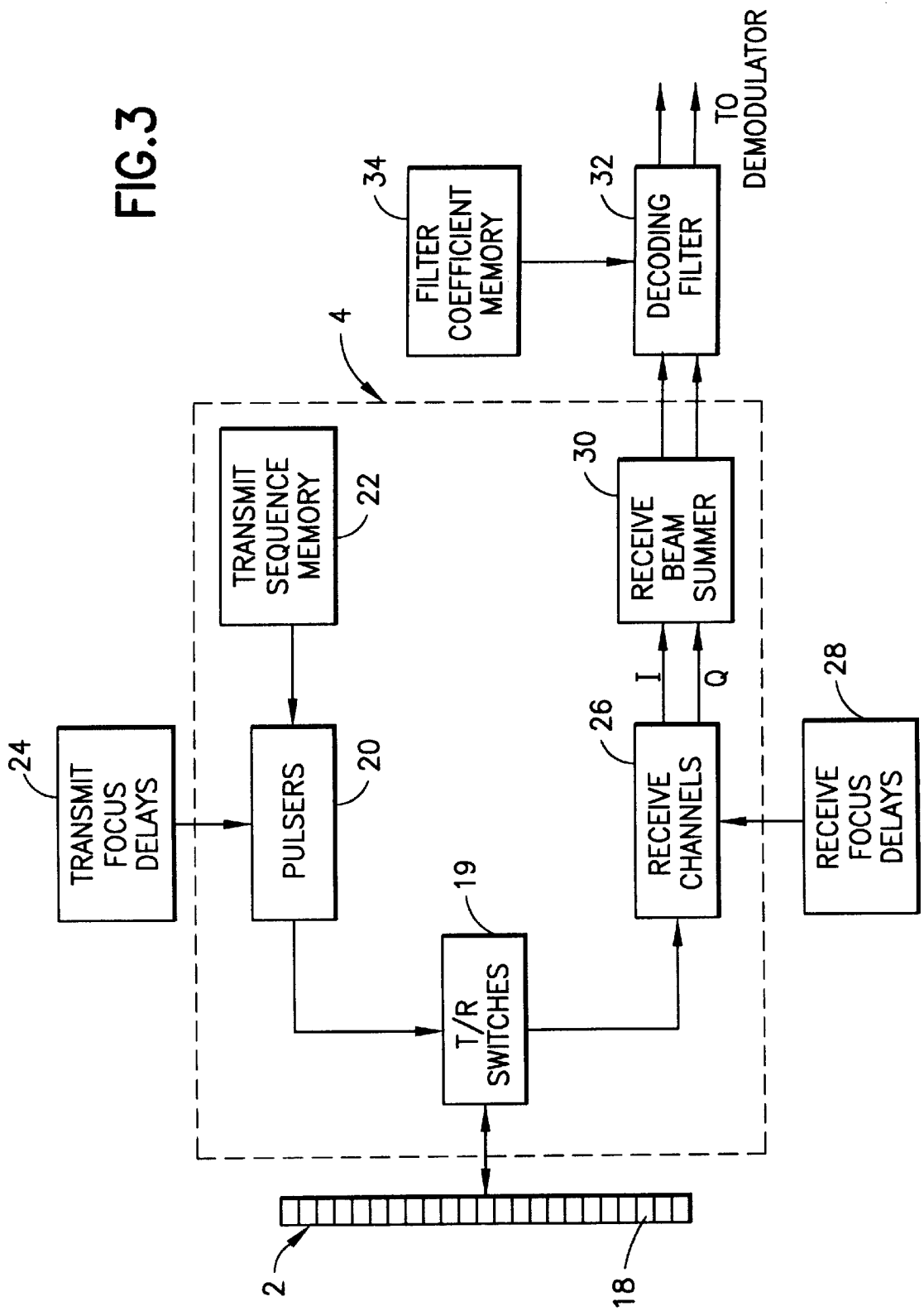

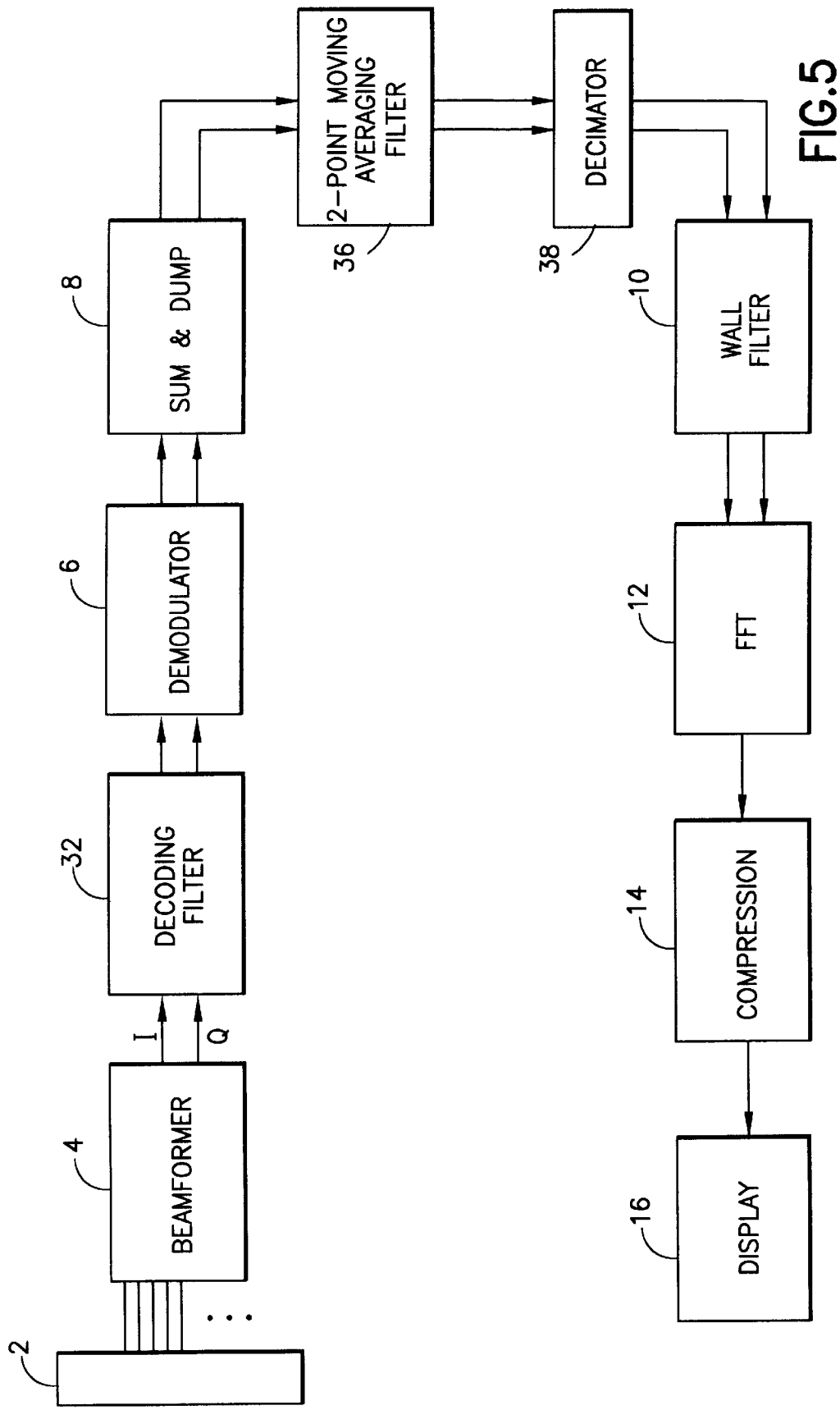

METHOD AND APPARATUS FOR PULSED DOPPLER IMAGING USING CODED EXCITATION ON TRANSMIT AND PULSE COMPRESSION ON RECEIVE

FIELD OF THE INVENTION

This invention relates to ultrasonic diagnostic systems which measure the velocity of blood flow using spectral Doppler techniques. In particular, the invention relates to the continuous display of blood velocity information.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency shift translates into the velocity of the blood flow.

In state-of-the-art ultrasonic scanners, the pulsed or continuous wave (CW) Doppler waveform is computed and displayed in real-time as a gray-scale spectrogram of velocity versus time with the gray-scale intensity (or color) modulated by the spectral power. The data for each spectral line comprises a multiplicity of frequency data bins for different frequency intervals, the spectral power data in each bin for a respective spectral line being displayed in a respective pixel of a respective column of pixels on the display monitor. Each spectral line represents an instantaneous measurement of blood flow.

FIG. 1 is a block diagram of the basic signal processing chain in a conventional spectral Doppler mode. An ultrasound transducer array 2 is activated to transmit by a transmit ultrasound burst of length P which is fired repeatedly at a pulse repetition frequency (PRF). The PRF is typically in the kilohertz range. The return RF signals are detected by the transducer elements and received by the respective receive channels in the beamformer 4. The beamformer sums the delayed channels data and outputs either RF or in-phase and quadrature (I/Q) data. The latter alternative is illustrated in FIG. 1.

The output of the beamformer is shifted in frequency by a demodulator 6. One way of achieving this is to multiply the input signal by a complex sinusoidal $e^{i2\pi f_d t}$, where $f_d$ is the frequency shift required. The demodulated I/Q components are integrated (summed) over a specific time interval T and then sampled at the PRF by a so-called "sum & dump" block 8. The summing interval and transmit burst length together define the length of the sample volume as specified by the user. The "sum and dump" operation effectively yields the Doppler signal backscattered from the sample volume. The resultant "slow time" Doppler signal samples are passed through a wall filter 10 which rejects any clutter corresponding to stationary or very slow-moving tissue. The filtered output is then fed into a spectrum analyzer 12, which typically takes Fast Fourier Transforms (FFTs) over a moving time window of 64 to 128 samples. Each FFT power spectrum is compressed (block 14) for display on a monitor 16 as a single spectral line at a particular time point in the Doppler velocity (frequency) versus time spectrogram.

One of the primary advantages of Doppler ultrasound is that it can provide noninvasive and quantitative measurements of blood flow in vessels. Given the angle θ between the insonifying beam and the flow axis, which is usually specified by rotating a cursor line in the B-mode image of a duplex scan, the magnitude of the velocity vector can be determined by the standard Doppler equation:

$$v = c f_d / (2 f_0 \cos \theta)$$

where c is the speed of sound in blood, $f_0$ is the transmit frequency and $f_d$ is the motion-induced Doppler frequency shift in the backscattered ultrasound. In practice an intensity-modulated Doppler frequency versus time spectrogram is displayed since the Doppler sample volume or range cell generally contains a distribution of velocities that can vary with time.

The summing interval T and the transmit burst length P together define the axial sensitivity profile of the user-select sample volume. In other words, the "sum & dump" operation yields the Doppler signal back-scattered from the sample volume. The summer, which is often referred to as the "range gate," is essentially a moving averager. This implies that the duration of the Doppler sensitivity interval is given by the convolution of the transmit burst and the range gate, as illustrated in FIG. 2. The axial length of the sample volume is then given by c(P+T)/2. For the purpose of this analysis, one can ignore the finite-bandwidth transducer effect on the idealized axial sensitivity profile of FIG. 2.

For a given Doppler scan geometry and system noise floor, the sensitivity to blood flow generally depends on the size of the sample volume (how much blood is insonified), the amplitude of the transmit burst (strength of insonification) and the P/T ratio. In accordance with optimal detection theory, for a given acoustic dosage the signal-to-noise ratio (SNR) is maximized when P/T=1, i.e., when the range gate is matched to the transmit burst. As indicated by the dashed lines in FIG. 2, this results in a triangular sample volume shape with maximum peak amplitude.

If a large sample volume is used to interrogate a shallow vessel, the parameters P, T and PRF can be so large (relative to B-mode) that Doppler sensitivity is not an issue. In fact, in such cases the Doppler sensitivity is probably already at its maximum allowed by the regulation dosage. In general, there is room for sensitivity improvement only in cases where the acoustic dosage is below regulation limit. For example, if one wants to interrogate a deep-lying vessel using a small sample volume, the longer round trip time will automatically limit the PRF to lower values. Together with an increased tissue attenuation factor, the acoustic dosage can fall below regulation limit at the sample volume position. If the user selects a small sample volume because he or she wants to avoid pickup from adjacent vessels or clutter sources, or to just examine a small region of interest (ROI) within the vessel of interest, then the transmit burst length P must be limited as well. To maximize the acoustic dosage, the transmit amplitude can be increased, but this may not always be possible due to the finite voltage limit of the pulser. In the worst cases, the flow signal may be too weak to be detected. In practice, this may force the user to forgo spatial resolution by increasing the sample volume size to 5 mm or longer in order to transmit a burst having increased length P and higher power (and using a longer range gate T).

Thus, there is a need for a method of improving pulsed Doppler sensitivity and/or sample volume resolution in such cases.

SUMMARY OF THE INVENTION

The present invention is a pulsed Doppler technique which uses coded excitation on transmit and pulse compression on receive. Coded excitation allows a long transmit pulse to be compressed on receive such that most energy is concentrated in a short interval. This technique can be used to maximize Doppler sensitivity of a small but deep-lying sample volume. Alternatively, for a given transmit acoustic burst length and dosage, the sample volume can be reduced to achieve better spatial resolution without compromising sensitivity.

The basic concept of the invention comprises modulating a specially designed code sequence based on a transmit burst (base sequence) of length P. The frequency of the transmit burst is typically in the megahertz range. A coded pulse sequence of N bursts is often referred to as an N-chip code. The coded pulse sequence, which has a length N×P, enables a larger acoustic dosage to be used to interrogate the flowing blood. The output from the beamformer is compressed in time by passing it through a decoding finite impulse response (FIR) filter. Some coded waveforms are best compressed by matched filtering, i.e., using a set of FIR filter coefficients that is an identical copy of the N-chip code. However, sometimes more desirable compression effects are achieved by mismatched filtering using FIR filters that have more than N filter coefficients or have coefficients which differ from the original N-chip code. The output of the decoding (i.e., compression) filter is a compressed signal pulse of length equal or close to the original transmit burst length P, but whose amplitude is that produced by the N-times-longer coded pulse sequence.

In accordance with the broad concept of the invention, the beamformer output can be either an RF signal or its I/Q components. Preferably, the beamformer output is decoded and then demodulated. If demodulation precedes decoding, then the decoding filter must be designed to compress the demodulated signal.

BRIEF DESCRIPTION OF THE DRAWINGS

FIG. 3 is a block diagram showing a portion of a spectral Doppler imaging system in accordance with a preferred embodiment of the invention.

FIG. 5 is a block diagram showing a spectral Doppler imaging system using Golay coded excitation in accordance with another preferred embodiment of the invention.

DETAILED DESCRIPTION OF THE PREFERRED EMBODIMENTS

Figure 1:
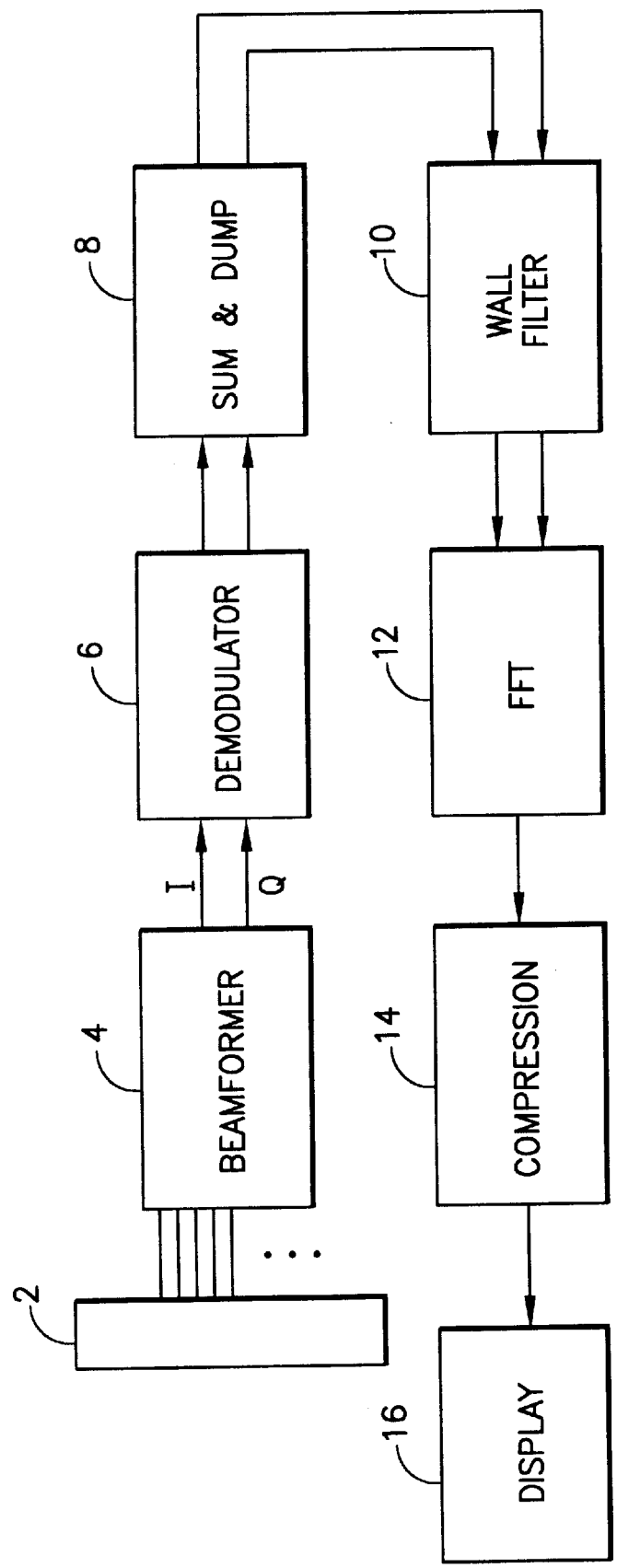
FIG. 1 is a block diagram showing the signal processing chain for a conventional spectral Doppler imaging system. I and Q denote the in-phase and quadrature components output by the beamformer.

The preferred embodiment of the invention is shown in FIG. 3. In this system each transducer element 18 in the transmit aperture by a coded pulse sequence derived from a coded transmit sequence formed by convolving a transmit code (e.g., a Barker code) with a base sequence (e.g., a tone burst). For an N-digit transmit code, the coded pulse sequence comprises N chips. In the simplest case, a bipolar pulser can be used to generate a polarity-coded pulse sequence in which the phase of pulses encoded with a +1 is 0°, while the phase of pulses encoded with a −1 is 180°. The coded transmit sequence for controlling the phase of pulses output by each bipolar pulser 20 is stored in a transmit sequence memory 22.

The bipolar pulsers 20 drive the elements 18 of transducer array 2 such that the ultrasonic energy produced is focused in a beam for each transmit firing. To accomplish this, transmit focus time delays 24 are imparted to the respective pulsed waveforms output by the pulsers in response to the coded transmit sequence. By appropriately adjusting the transmit focus time delays in a conventional manner, the ultrasonic beam can be focused at a desired transmit focal position. The coded pulse sequences are sent from the pulsers to the transducer elements via respective transmit/ receive (T/R) switches 19. The T/R switches 19 are typically diodes which protect the receive electronics from the high voltages generated by the transmit electronics. The transmit signal causes the diodes to shut off or limit the signal to the receiver.

After each transmit, the echo signals detected by the transducer elements 18 are fed to respective receive channels 26 of the receive beamformer, also via the T/R switches 19. The receive beamformer tracks echoes under the direction of a master controller (not shown). The receive beamformer imparts the proper receive focus time delays 28 to the received echo signal and sums them to provide an echo signal which accurately indicates the total ultrasonic energy reflected from a succession of ranges corresponding to a particular transmit focal position. The beamformer also transforms the RF signal into its I/Q components by means of Hilbert bandpass filtering. The I/Q components are then summed in receive summer 30 for each transmit firing. Although FIG. 3 depicts Hilbert bandpass filtering as occurring in receive channels 26, it will be appreciated that Hilbert bandpass filtering can alternatively be performed after beam summation.

The I/Q components for each transmit firing are then decoded by a respective decoding filter 32 which outputs a compressed pulse in accordance with the present invention. The appropriate decoding filter is designed based on the transmit code, the demodulation frequency (if decoding follows demodulation) and the amount of downsampling performed on receive. For an N-digit transmit code, each decoding filter 32 is preferably an FIR filter having M filter taps (M≧N) for receiving a set of M filter coefficients from a filter coefficient memory 34. In accordance with a preferred embodiment, the filter coefficients $c_0, c_1, \ldots, C_{M-1}$ have scalar values which, when convolved with the N-digit transmit code, produce a compressed receive pulse sequence. [The filter coefficients, like the transmit and receive time delays and the coded transmit sequences, can be supplied by the master controller.] Filter 32 outputs the pulse compressed signal to the demodulator 6 (see FIG. 5).

Figure 4:
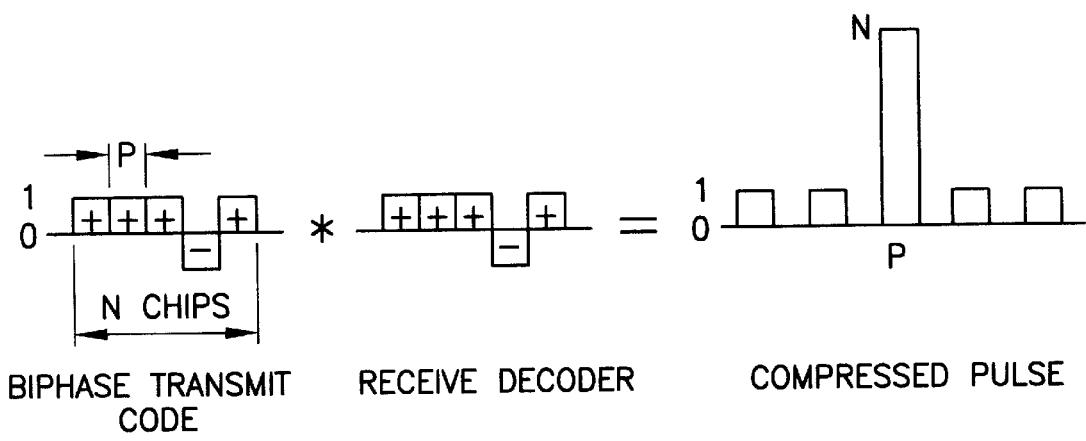
FIG. 4 is a schematic illustrating a compressed pulse resulting from convolution of a biphase transmit code with a matching compression code.

As an example, FIG. 4 shows a 5-chip code sequence from the Barker code family. Barker codes are biphase (or binary) code sequences of various lengths up to N=13. [The set of all Barker codes is disclosed in an article by Welch et al. entitled "Sidelobe suppressed spread spectrum pulse compression for ultrasonic tissue imaging," IEEE Trans Ultrasonics, Ferroelec., and Freq. Control (accepted for publication, August 1997), the contents of which are incorporated by reference herein.] If the 5-bit Barker code is decoded by a matching FIR filter (i.e., a filter having filter coefficients identical to the digits of the transmit code) as shown in FIG. 4, the compression ratio achieved is N=5, which corresponds to a SNR gain of 7 dB. However, as seen in FIG. 4, the main pulse in the decoder filter output is surrounded by pulses of smaller amplitude. These small-amplitude pulses correspond to axial or range sidelobes that are 1/N times lower in amplitude compared to the main lobe.

Among all biphase codes, Barker codes are well known for their property of having the smallest sidelobes possible when decoded by a matched filter. However, it should be noted that for any single transmit code, the sidelobes can often be suppressed via mismatched filtering at the expense of decreased signal gain and/or main lobe broadening (decreased range resolution). An example of a mismatched filter for the 5-bit Barker code shown in FIG. 4 is a 10-tap FIR filter whose coefficients are as follows: [−0.304, −0.006, 0.722, −1.223, 0.798, 1.253, 0.722, 0.046, −0.304, −0.260]. The coefficients of this mismatched filter were determined using a well-known least squares technique [see, e.g., Robinson et al., Geophysical Signal Analysis, Englewood Cliffs, Prentice-Hall (1980)] to minimize the sidelobes while trying to preserve the peak spike. It can be shown that this particular 10-tap decoding filter yields a 6.5-dB sidelobe suppression with only a 0.5-dB reduction in signal gain, relative to that produced using the matched filter of FIG. 4. In general, greater sidelobe suppression can be achieved using longer mismatched FIR filters. As discussed hereinafter, instead of using very long mismatched filters, strong sidelobe suppression is also possible utilizing two- or multiple-transmit complementary codes.

For the same total transmit energy, coded excitation techniques may also enable sample volumes that are significantly smaller than 1–2 mm (conventional limits) to be generated, which may be useful for high-frequency interrogation of very small and shallow vessels. This may become especially important for two-dimensional transducer arrays that can provide tight beam control in the plane orthogonal to the beam axis.

Standard codes such as the Barker code and chirp, which only require a single firing to realize pulse compression, have been previously proposed for B-mode imaging. While the prior art has alluded to the fact that some codes (e.g., polyphase) are more tolerant to motion-induced Doppler shifts, the main caveat is that the range sidelobes after compression can be quite high (say, −20 to −30 dB depending on the decoder length), such that the resultant degradation in contrast resolution becomes unacceptable for B-mode imaging in which the display dynamic range is typically greater than 60 dB. To address this problem, a heavily apodized chirped excitation has been proposed in the prior art.

Figure 2:
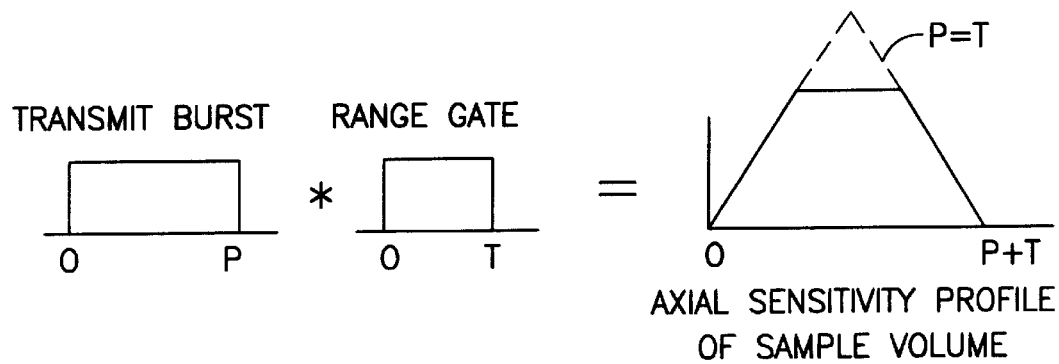
FIG. 2 is a schematic illustrating the axial sensitivity profile of a sample volume resulting from convolution of a transmit burst of length P with a range gate T.

For pulsed Doppler applications, however, the presence of range sidelobes below −20 dB is not an issue since the sample volume size is typically defined by the −20 dB points (or higher) and the spectrum display dynamic range is usually set at 25–35 dB only. The reason is that pulsed Doppler is aimed at measuring the flow velocity distribution within the sample volume, and not spatial imaging. In fact, as illustrated in FIG. 2, the shape of the sample volume in conventional Doppler techniques may vary from a rectangular or trapezoidal to a triangular shape, depending on the P/T ratio. Further, a relatively sharp high-pass filter is often used to reject stationary or slow-moving clutter that may be picked up by sidelobes of the sensitivity volume. Hence, standard codes based on a single firing should be suitable for pulsed Doppler imaging.

To implement coded excitation on a digital ultrasound scanner, the encoding on transmit can be realized simply by convolving a transmit code with the desired base sequence (e.g., [1,−1,1,−1]). For example, if a biphase code like that shown in FIG. 4 is used, the base sequence is simply repeated N times, but with possible sign changes (or 180° phase shifts) as dictated by the transmit code. For example, when the Barker code [1,1, 1,−1,1] is applied to a base sequence [1,−1,1,−1], the coded transmit sequence [1,−1, 1,−1] [1,−1,1,−1] [1,−1, 1,−1] [−1,1,−1,1] [1,−1,1,−1] will be produced. On receive, the demodulated signal is compressed in time via the decoding FIR filter whose coefficients may be matched exactly to the transmit code [1,1,1,−1,1] (as shown in FIG. 4), or by mismatched filtering. For example, for the Barker code [1,1,1,−1,1], a matching FIR filter having five filter taps can be used, each filter tap receiving a respective digit of the Barker code, with the filter tap intervals corresponding to P or the chip duration prior to the decoding filter if downsampling has been applied. After decoding, the signal processing can proceed as shown in FIG. 1 and the summer length T can be set as if the actual transmit burst length used were P.

The decoding FIR filter 32 can be implemented in software or hardware at the beamformer output, as shown in FIG. 3, or at the demodulator output. In the latter case, the decoding filter coefficients must be matched or mismatched to the demodulated signals. The demodulator multiplies the input by a complex sinusoidal $e^{i2\pi f_d t}$, where $f_d$ is the frequency shift required to bring the signal spectrum to baseband. For the case when the demodulator shifts by discrete frequencies $f_d = n/2t_b$, where n is any positive integer and $t_b$ is the duration of the transmit base sequence, the sinusoidal becomes real and the same set of filter coefficients are input to both decoding filters for the I and Q components, which thus form a real filter. In the cases when $f_d \neq n/2t_b$, the I and Q decoding filters receive different sets of filter coefficients and thus form a complex filter. In the latter case, the filter coefficients are either matched or mismatched to the respective demodulated signal component.

If for some application the range sidelobes associated with the above single-firing codes are unacceptable, one can resort to an alternative technique known as Golay coding. In the case of Golay code pairs, the Golay coding consists of two complementary codes that are fired one after another along the same beam. In particular, the set of Golay codes includes complementary Barker codes. For example, the 4-digit Barker code [1,−1,1,1] has a special feature which enables one not only to eliminate sidelobes, but to build codes of great length. This code, and also the 2-digit Barker code [1,−1], have complementary forms. Corresponding sidelobes produced by a pair of complementary codes have opposite phases. Therefore, if one alternately modulates successive transmitted pulses with the two complementary codes, when the return signals from successive pulses are summed the sidelobes cancel. In actual implementation, a transmit sequence alternating between the two complementary codes is fired, received, decoded, demodulated and then passed through the "sum & dump" block 8 as shown in FIG. 5. The output is a sequence of alternating "slow-time" samples that are associated with range sidelobes of opposite polarities. These alternating "slow-time" samples can be summed to cancel out the range sidelobes simply by convolving with an FIR filter 36 using filter coefficients [0.5, 0.5], i.e., taking a two-point moving average of the alternating slow-time samples, and then decimating the averager output by a factor of two (block 38 in FIG. 5). The result is then passed through a wall filter 10 followed by FFT spectrum analysis. The two-point moving averager 36 can be implemented in either software or hardware before the wall filter 10 in FIG. 5.

To demonstrate the use of Golay codes on transmit and pulse compression on receive, the following example is given. Golay coding on transmit can be realized simply by convolving the Golay code with the desired base sequence (e.g., [1,-1,1,-1]). If the Golay code pairs [1,-1,1,1] and [1,-1,-1,-1] are used, the transmit base sequence is simply repeated, but with sign changes (or 180° phase shifts) as dictated by the Golay code [1,-1,1,1] on the odd-numbered transmits and by the Golay code [1,-1,-1,-1] on the even-numbered transmits. For example, when the Golay code [1,-1,1,1] is applied to the base sequence [1,-1,1,-1] for a first transmit firing, the coded transmit sequence [1,-1,1,-1] [-1,1, -1,1] [1,-1,1,-1] [1,-1,1,-1] will be produced. On receive, the beamsummed signals generated by the first transmit firing are each compressed in time via respective decoding FIR filters whose coefficients may be matched exactly to the transmit code [1,-1,1,1]. When the Golay code [1,-1,-1,-1] is applied to the base sequence [1,-1,1,-1] for a second transmit firing, the coded pulse sequence [1,-1,1,-1] [-1,1,-1,1] [-1,1,-1,1] [-1,1,-1,1] will be produced. On receive, the beamsummed signals generated by the second transmit firing are each compressed in time via the respective decoding FIR filters whose coefficients may be matched exactly to the transmit code [1,-1,-1,-1]. When the compressed signals resulting from the first and second transmit firings are averaged or summed, the range sidelobes are cancelled.

The foregoing preferred embodiments have been disclosed for the purpose of illustration. Variations and modifications of the concept of the invention will be readily apparent to persons skilled in the art. In particular, the invention encompasses the use of any Golay or complementary codes and is not limited to using complementary Barker codes only. Furthermore, although the preferred embodiments employ binary complementary codes, it will be appreciated by persons skilled in the art that the transmit pulse sequences may be amplitude-coded, rather than phase- or polarity-coded. In addition, polyphase codes can be used in place of biphase codes. All such variations and modifications are intended to be encompassed by the claims set forth hereinafter.

We claim:

1. A system for estimating and displaying Doppler frequency shifts produced by moving ultrasound scatterers, comprising:

an ultrasound transducer array for transmitting ultrasound waves and detecting ultrasound echoes reflected by said ultrasound scatterers, said transducer array comprising a multiplicity of transducer elements;

transmit means coupled to said transducer array for pulsing selected transducer elements which form a transmit aperture with a coded pulse sequence during first and second transmit firings which are focused at substantially the same transmit focal position, said coded pulse sequence being a function of a transmit code convolved with a base pulse sequence;

receive means coupled to said transducer array for receiving first and second sets of signals from selected transducer elements which form a receive aperture subsequent to said first and second transmit firings respectively;

means for forming a first and second beamsummed signals respectively derived from said first and second sets of signals;

a decoding filter for compressing said first and second beamsummed signals to form first and second compressed pulse sequences respectively;

processing means for producing a set of Doppler frequency shift data which is dependent in part on said first and second compressed pulse sequences; and means for displaying a spectral line which is a function of said set of Doppler frequency shift data.

2. The system as defined in claim 1, wherein said filtering means are programmed with a first set of filter coefficients which match said first transmit code.

3. The system as defined in claim 1, wherein said filtering means are programmed with a first set of filter coefficients which are mismatched with said first transmit code.

4. The system as defined in claim 1, wherein said filtering means comprise an FIR filter.

5. The system as defined in claim 1, wherein said first transmit code is a Barker code.

6. The system as defined in claim 1, wherein:

said transmit means pulse said selected transducer elements which form said transmit aperture with a second coded pulse sequence during third and fourth transmit firings, said second coded pulse sequence being a function of a second transmit code convolved with said base sequence, said first and second transmit codes being members of a complementary code set, and said third and fourth transmit firings being focused at substantially said same transmit focal position;

said receive means receive third and fourth sets of signals from said selected transducer elements which form said receive aperture subsequent to said third and fourth transmit firings;

said forming means form third and fourth beamsummed signals respectively derived from said third and fourth sets of signals;

said filtering means compress said third and fourth beamsummed signals to form third and fourth compressed pulse sequences respectively; and said set of Doppler frequency shift data is dependent in part on said third and fourth compressed pulse sequences.

7. The system as defined in claim 6, wherein said processing means comprise adding means for adding said first and third compressed pulse sequences together and adding said second and fourth compressed pulse sequences together.

8. The system as defined in claim 7, wherein said adding means comprise a two-point moving average filter and a decimator coupled to said two-point moving average filter.

9. The system as defined in claim 6, wherein said filtering means are programmed with a first set of filter coefficients which match said first transmit code during said first transmit firing and with a second set of filter coefficients which match said second transmit code during said second transmit firing.

10. The system as defined in claim 6, wherein said first and second transmit codes are Golay codes.

11. A method for estimating and displaying Doppler frequency shifts produced by moving ultrasound scatterers, comprising the steps of:

producing a first coded pulse sequence which is a function of a first transmit code convolved with a base pulse sequence;

driving a first set of transducer elements forming a transmit aperture in a transducer array with said first coded pulse sequence during a first transmit firing;

receiving a first set of echo signals from a second set of transducer elements forming a receive aperture in the transducer array subsequent to said first transmit firing;

forming a first beamsummed signal derived from said first set of echo signals;

compressing said first beamsummed signal to form a first compressed pulse sequence;

driving said first set of transducer elements forming said transmit aperture with said first coded pulse sequence during a second transmit firing, said first and second transmit firings being focused at substantially the same transmit focal position;

receiving a second set of echo signals from said second set of transducer elements forming said receive aperture subsequent to said second transmit firing;

forming a second beamsummed signal derived from said second set of echo signals;

compressing said second beamsummed signal to form a second compressed pulse sequence;

acquiring a set of Doppler frequency shift data which is dependent in part on said first and second compressed pulse sequences; and displaying a spectral line which is a function of said set of Doppler frequency shift data.

12. The method as defined in claim 11, wherein said first transmit code is a Barker code.

13. The method as defined in claim 11, wherein said compressing steps are carried out by filtering said first and second beamsummed signals using a first set of filter coefficients which match said first transmit code.

14. The method as defined in claim 11, wherein said compressing steps are carried out by filtering said first and second beamsummed signals using a first set of filter coefficients which are mismatched said first transmit code.

15. The method as defined in claim 11, further comprising the steps of:

producing a second coded pulse sequence which is a function of a second transmit code convolved with a base pulse sequence;

driving said first set of transducer elements forming said transmit aperture with said second coded pulse sequence during a third transmit firing, said third transmit firing being focused at substantially said same transmit focal position;

receiving a third set of echo signals from said second set of transducer elements forming said receive aperture subsequent to said third transmit firing;

forming a third beamsummed signal derived from said third set of echo signals;

compressing said third beamsummed signal to form a third compressed pulse sequence;

driving said first set of transducer elements forming said transmit aperture with said second coded pulse sequence during a fourth transmit firing, said fourth transmit firing being focused at substantially said same transmit focal position;

receiving a fourth set of echo signals from said second set of transducer elements forming said receive aperture subsequent to said fourth transmit firing;

forming a fourth beamsummed signal derived from said fourth set of echo signals;

compressing said fourth beamsummed signal to form a fourth compressed pulse sequence;

wherein said set of Doppler frequency shift data is dependent in part on said third and fourth compressed pulse sequences.

16. The method as defined in claim 15, wherein said compressing steps are carried out by filtering said first and second beamsummed signals using a first set of filter coefficients which match said first transmit code, and by filtering said third and fourth beamsummed signal using a second set of filter coefficients which match said second transmit code.

17. The method as defined in claim 15, wherein said first and second transmit codes are Golay codes.

18. The method as defined in claim 15, wherein said acquiring step comprises the steps of adding said first and third compressed pulse sequences together and adding said second and fourth compressed pulse sequences together.

19. A system for estimating and displaying Doppler frequency shifts produced by moving ultrasound scatterers, comprising:

an ultrasound transducer array for transmitting ultrasound waves and detecting ultrasound echoes reflected by said ultrasound scatterers, said transducer array comprising a multiplicity of transducer elements;

transmit means coupled to said transducer array for pulsing selected transducer elements which form a transmit aperture with a coded pulse sequence during first and second transmit firings which are focused at substantially the same transmit focal position, said coded pulse sequence being a function of a transmit code convolved with a base pulse sequence;

receive means coupled to said transducer array for receiving first and second sets of signals from selected transducer elements which form a receive aperture subsequent to said first and second transmit firings respectively;

means for forming a first and second beamsummed signals respectively derived from said first and second sets of signals;

means for demodulating said first and second beamsummed signals to form first and second demodulated signals respectively;

a decoding filter for compressing said first and second demodulated signals to form first and second compressed pulse sequences respectively;

processing means for producing a set of Doppler frequency shift data which is dependent in part on said first and second compressed pulse sequences; and means for displaying a spectral line which is a function of said set of Doppler frequency shift data.

20. The system as defined in claim 19, wherein said decoding filter is programmed with a set of filter coefficients which match said first demodulated signal.

21. The system as defined in claim 19, wherein said decoding filter is programmed with a set of filter coefficients which are mismatched to said first demodulated signal.

* * * * *